(12) United States Patent
Schlebusch et al.

(10) Patent No.: US 12,702,816 B2
(45) Date of Patent: Aug. 11, 2026

(54) IMPLANTABLE CARDIAC SUPPORT SYSTEM

(71) Applicant: KARDION GMBH, Stuttgart (DE)

(72) Inventors: Thomas Alexander Schlebusch, Renningen (DE); Michael Curcic, Stuttgart (DE)

(73) Assignee: Kardion GmbH, Stuttgart (DE)

( * ) Notice: Subject to any disclaimer, the term of this patent is extended or adjusted under 35 U.S.C. 154(b) by 925 days.

(21) Appl. No.: 17/266,068

(22) PCT Filed: Aug. 7, 2019

(86) PCT No.: PCT/EP2019/071204
§ 371 (c)(1),
(2) Date: Oct. 22, 2021

(87) PCT Pub. No.: WO2020/030686
PCT Pub. Date: Feb. 13, 2020

(65) Prior Publication Data

US 2022/0032032 A1 Feb. 3, 2022

(30) Foreign Application Priority Data

Aug. 7, 2018 (DE) ........................ 102018213151.1

(51) Int. Cl.

| | |
|---|---|
| ***A61M 60/139*** | (2021.01) |
| ***A61M 60/178*** | (2021.01) |
| ***A61M 60/216*** | (2021.01) |
| ***A61M 60/411*** | (2021.01) |
| ***A61M 60/523*** | (2021.01) |

(52) U.S. Cl.
CPC ........ *A61M 60/139* (2021.01); *A61M 60/178* (2021.01); *A61M 60/216* (2021.01); *A61M 60/411* (2021.01); *A61M 60/523* (2021.01); *A61M 2205/3375* (2013.01)

(58) Field of Classification Search
CPC ........... A61M 1/3659; A61B 8/06; A61B 8/12
See application file for complete search history.

(56) References Cited

U.S. PATENT DOCUMENTS

| | | | |
|---|---|---|---|
| 3,088,323 | A | 5/1963 | Welkowitz et al. |
| 4,023,562 | A | 5/1977 | Hynecek et al. |

(Continued)

FOREIGN PATENT DOCUMENTS

| | | |
|---|---|---|
| CA | 3 122 415 | 7/2020 |
| CN | 1192351 A | 9/1998 |

(Continued)

OTHER PUBLICATIONS

Hertz Ph.D. et al, “Ultrasonic Engineering in Heart Diagnosis”, The American Journal of Cardiology, Jan. 1967, vol. 19, No. 1, pp. 6-17.

(Continued)

*Primary Examiner* — Michael J D’Abreu
(74) *Attorney, Agent, or Firm* — Knobbe, Martens, Olson & Bear, LLP

(57) ABSTRACT

The invention relates to an implantable, vascular support system (10) having a cannula (13) and an ultrasound measuring device (18), wherein the cannula (13) and the ultrasound measuring device (18) are disposed in the region of mutually opposite ends of the support system (10).

11 Claims, 4 Drawing Sheets

(56) References Cited

U.S. PATENT DOCUMENTS 4,559,952 A 12/1985 Angelsen et al.
4,680,730 A 7/1987 Omoda
4,781,525 A 11/1988 Hubbard et al.
4,888,011 A 12/1989 Kung et al.
4,889,131 A 12/1989 Salem et al.
4,902,272 A 2/1990 Milder et al.
5,045,051 A 9/1991 Milder et al.
5,269,811 A 12/1993 Hayes
5,289,821 A 3/1994 Swartz
5,456,715 A 10/1995 Liotta
5,527,159 A 6/1996 Bozeman, Jr. et al.
5,581,038 A 12/1996 Lampropoulos
5,606,972 A * 3/1997 Routh ................ G01S 15/8979 600/455
5,613,935 A 3/1997 Jarvik
5,662,115 A 9/1997 Torp
5,676,651 A 10/1997 Larson, Jr. et al.
5,720,771 A 2/1998 Snell
5,752,976 A 5/1998 Duffin et al.
5,766,207 A 6/1998 Potter et al.
5,827,203 A 10/1998 Nita
5,865,759 A 2/1999 Koblanski
5,888,242 A 3/1999 Antaki et al.
5,904,708 A 5/1999 Goedeke
5,911,685 A 6/1999 Siess et al.
5,964,694 A 10/1999 Siess et al.
5,980,465 A 11/1999 Elgas
6,007,478 A 12/1999 Siess et al.
6,024,704 A 2/2000 Meador et al.
6,053,873 A 4/2000 Govari et al.
6,167,765 B1 1/2001 Weitze
6,176,822 B1 1/2001 Nix et al.
6,183,412 B1 2/2001 Benkowsi et al.
6,185,460 B1 2/2001 Thompson
6,190,324 B1 2/2001 Kieval et al.
6,210,318 B1 4/2001 Lederman
6,231,498 B1 5/2001 Pfeiffer et al.
6,245,007 B1 6/2001 Bedingham et al.
6,314,322 B1 11/2001 Rosenberg
6,351,048 B1 2/2002 Schob et al.
6,398,734 B1 * 6/2002 Cimochowski .......... A61B 8/12 600/459
6,432,136 B1 8/2002 Weiss et al.
6,438,409 B1 8/2002 Malik et al.
6,512,949 B1 1/2003 Combs et al.
6,530,876 B1 3/2003 Spence
6,540,658 B1 4/2003 Fasciano et al.
6,540,659 B1 4/2003 Milbocker
6,561,975 B1 5/2003 Pool et al.
6,579,257 B1 6/2003 Elgas et al.
6,602,182 B1 8/2003 Milbocker
6,605,032 B2 8/2003 Benkowsi et al.
6,652,447 B2 11/2003 Benkowsi et al.
6,731,976 B2 5/2004 Penn et al.
6,879,126 B2 4/2005 Paden et al.
6,912,423 B2 6/2005 Ley et al.
6,949,066 B2 9/2005 Bearnson et al.
6,984,201 B2 1/2006 Khaghani et al.
7,010,954 B2 3/2006 Siess
7,022,100 B1 4/2006 Aboul-Hosn et al.
7,024,244 B2 4/2006 Muhlenberg et al.
7,070,555 B2 7/2006 Siess
7,083,588 B1 8/2006 Shmulewitz et al.
7,138,776 B1 11/2006 Gauthier et al.
7,160,243 B2 1/2007 Medvedev
7,175,588 B2 2/2007 Morello
7,177,681 B2 2/2007 Xhu
7,238,151 B2 7/2007 Frazier
7,396,327 B2 7/2008 Morello
7,513,864 B2 4/2009 Kantrowitz et al.
7,520,850 B2 4/2009 Brockway
7,526,338 B1 4/2009 Gill
7,527,599 B2 5/2009 Hickey
7,591,777 B2 9/2009 LaRose
7,744,560 B2 6/2010 Struble
7,794,384 B2 9/2010 Sugiura et al.
7,819,916 B2 10/2010 Yaegashi
7,850,593 B2 12/2010 Vincent et al.
7,850,594 B2 12/2010 Sutton et al.
7,856,335 B2 12/2010 Morello et al.
7,862,501 B2 1/2011 Woodward et al.
7,951,062 B2 5/2011 Morello
7,951,129 B2 5/2011 Chinchoy
7,963,905 B2 6/2011 Salmonsen et al.
7,988,728 B2 8/2011 Ayre
8,075,472 B2 12/2011 Zilbershlag et al.
8,190,390 B2 5/2012 Morello et al.
8,211,028 B2 7/2012 Karamanoglu et al.
8,303,482 B2 11/2012 Schima et al.
8,323,173 B2 12/2012 Benkowsi et al.
8,435,182 B1 5/2013 Tamura
8,449,444 B2 5/2013 Poirier
8,545,380 B2 10/2013 Farnan et al.
8,585,572 B2 11/2013 Mehmanesh
8,591,393 B2 11/2013 Walters et al.
8,594,790 B2 11/2013 Kjellstrom et al.
8,622,949 B2 1/2014 Zafirelis et al.
8,657,733 B2 2/2014 Ayre et al.
8,657,875 B2 2/2014 Kung et al.
8,715,151 B2 5/2014 Poirier
8,747,293 B2 6/2014 Arndt et al.
8,849,398 B2 9/2014 Evans
8,864,643 B2 10/2014 Reichenbach et al.
8,864,644 B2 10/2014 Yomtov
8,876,685 B2 11/2014 Crosby et al.
8,882,477 B2 11/2014 Fritz, IV et al.
8,888,728 B2 11/2014 Aboul-Hosn et al.
8,897,873 B2 11/2014 Schima et al.
8,903,492 B2 12/2014 Soykan et al.
9,091,271 B2 7/2015 Bourque
9,297,735 B2 3/2016 Graichen et al.
9,308,305 B2 4/2016 Chen et al.
9,345,824 B2 5/2016 Mohl et al.
9,371,826 B2 6/2016 Yanai et al.
9,427,508 B2 8/2016 Reyes et al.
9,427,509 B2 8/2016 Vodermayer
9,474,840 B2 10/2016 Siess
9,492,601 B2 11/2016 Casas et al.
9,511,179 B2 12/2016 Casas et al.
9,555,173 B2 1/2017 Spanier
9,555,175 B2 1/2017 Bulent et al.
9,556,873 B2 1/2017 Yanai et al.
9,566,374 B2 2/2017 Spence et al.
9,636,442 B2 5/2017 Karmon et al.
9,656,010 B2 5/2017 Burke
9,669,142 B2 6/2017 Spanier et al.
9,669,144 B2 6/2017 Spanier et al.
9,694,123 B2 7/2017 Bourque et al.
9,713,701 B2 7/2017 Sarkar et al.
9,744,282 B2 8/2017 Rosenberg et al.
9,789,236 B2 10/2017 Bonde
9,833,550 B2 12/2017 Siess
9,848,899 B2 12/2017 Sliwa et al.
9,849,224 B2 12/2017 Angwin et al.
9,878,087 B2 1/2018 Richardson et al.
9,943,236 B2 4/2018 Bennett et al.
9,950,102 B2 4/2018 Spence et al.
9,974,894 B2 5/2018 Morello
9,999,714 B2 6/2018 Spanier et al.
10,010,662 B2 7/2018 Wiesener et al.
10,022,480 B2 7/2018 Greatrex et al.
10,029,037 B2 7/2018 Muller et al.
10,052,420 B2 8/2018 Medvedev et al.
10,279,093 B2 5/2019 Reichenbach et al.
10,322,217 B2 6/2019 Spence
10,342,906 B2 7/2019 D'Ambrosio et al.
10,350,342 B2 7/2019 Thomas et al.
10,357,598 B2 7/2019 Aboul-Hosn et al.
10,376,162 B2 8/2019 Edelman et al.
10,413,651 B2 9/2019 Yomtov et al.
10,426,879 B2 10/2019 Farnan
10,449,275 B2 10/2019 Corbett
10,500,322 B2 12/2019 Karch
10,525,178 B2 1/2020 Zeng

(56) References Cited

U.S. PATENT DOCUMENTS 10,549,020 B2 2/2020 Spence et al.
10,561,771 B2 2/2020 Heilman et al.
10,561,772 B2 2/2020 Schumacher
10,561,773 B2 2/2020 Ferrari et al.
10,632,241 B2 4/2020 Schenck et al.
10,660,998 B2 5/2020 Hodges
10,668,195 B2 6/2020 Flores
10,732,583 B2 8/2020 Rudser
10,857,275 B2 12/2020 Granegger
10,864,308 B2 12/2020 Muller et al.
11,027,114 B2 6/2021 D'Ambrosio et al.
RE48,649 E 7/2021 Siess
11,067,085 B2 7/2021 Granegger et al.
11,120,908 B2 9/2021 Agnello et al.
11,131,968 B2 9/2021 Rudser
11,147,960 B2 10/2021 Spanier et al.
11,154,701 B2 10/2021 Reyes et al.
11,154,702 B2 10/2021 Kadrolkar et al.
11,185,682 B2 11/2021 Farnan
11,191,945 B2 12/2021 Siess et al.
11,197,618 B2 12/2021 Edelman et al.
11,217,344 B2 1/2022 Agnello
11,235,139 B2 2/2022 Kudlik
11,241,572 B2 2/2022 Dague et al.
11,273,299 B2 3/2022 Wolman et al.
11,285,310 B2 3/2022 Curran et al.
11,285,311 B2 3/2022 Siess et al.
11,298,524 B2 4/2022 El Katerji et al.
11,311,711 B2 4/2022 Casas et al.
11,316,679 B2 4/2022 Agnello
11,320,382 B2 5/2022 Aikawa
11,324,395 B2 5/2022 Banik et al.
11,331,082 B2 5/2022 Itoh et al.
11,337,724 B2 5/2022 Masubuchi et al.
11,338,125 B2 5/2022 Liu et al.
11,351,356 B2 6/2022 Mohl
11,351,357 B2 6/2022 Mohl
11,351,358 B2 6/2022 Nix et al.
11,357,438 B2 6/2022 Stewart et al.
11,357,968 B2 6/2022 El Katerji et al.
11,376,415 B2 7/2022 Mohl
11,376,419 B2 7/2022 Reyes et al.
11,389,639 B2 7/2022 Casas
11,389,641 B2 7/2022 Nguyen et al.
11,413,444 B2 8/2022 Nix et al.
11,413,445 B2 8/2022 Brown et al.
11,420,041 B2 8/2022 Karch
11,439,806 B2 9/2022 Kimball et al.
11,446,481 B2 9/2022 Wolman et al.
11,478,629 B2 10/2022 Harjes et al.
11,517,740 B2 12/2022 Agarwa et al.
11,521,723 B2 12/2022 Liu et al.
11,524,165 B2 12/2022 Tan et al.
11,527,322 B2 12/2022 Agnello et al.
11,529,062 B2 12/2022 Moyer et al.
11,554,260 B2 1/2023 Reyes et al.
11,572,879 B2 2/2023 Mohl
11,574,741 B2 2/2023 Tan et al.
11,577,068 B2 2/2023 Spence et al.
11,581,083 B2 2/2023 El Katerji et al.
11,583,659 B2 2/2023 Pfeffer et al.
11,587,337 B2 2/2023 Lemay et al.
11,590,337 B2 2/2023 Granegger et al.
11,622,695 B1 4/2023 Adriola et al.
11,628,293 B2 4/2023 Gandhi et al.
11,639,722 B2 5/2023 Medvedev et al.
11,648,386 B2 5/2023 Poirer
11,653,841 B2 5/2023 Reyes et al.
11,666,746 B2 6/2023 Ferrari et al.
11,668,321 B2 6/2023 Richert et al.
11,674,517 B2 6/2023 Mohl
11,676,718 B2 6/2023 Agnello et al.
11,684,276 B2 6/2023 Cros et al.
11,684,769 B2 6/2023 Harjes et al.
11,694,539 B2 7/2023 Kudlik et al.
11,694,813 B2 7/2023 El Katerji et al.
11,696,782 B2 7/2023 Carlson et al.
11,707,617 B2 7/2023 Reyes et al.
11,712,167 B2 8/2023 Medvedev et al.
11,724,091 B2 8/2023 Siess et al.
11,754,077 B1 9/2023 Mohl
D1,001,145 S 10/2023 Lussier et al.
D1,001,146 S 10/2023 Lussier et al.
11,771,885 B2 10/2023 Liu et al.
11,779,234 B2 10/2023 Harjes et al.
11,781,551 B2 10/2023 Yanai et al.
11,790,487 B2 10/2023 Barbato et al.
11,793,994 B2 10/2023 Josephy et al.
11,806,116 B2 11/2023 Tuval et al.
11,806,517 B2 11/2023 Petersen
11,806,518 B2 11/2023 Michelena et al.
11,813,079 B2 11/2023 Lau et al.
11,818,782 B2 11/2023 Doudian et al.
11,824,381 B2 11/2023 Conyers et al.
11,826,127 B2 11/2023 Casas
11,832,793 B2 12/2023 McWeeney et al.
11,832,868 B2 12/2023 Smail et al.
11,837,364 B2 12/2023 Lee et al.
11,844,592 B2 12/2023 Tuval et al.
11,844,940 B2 12/2023 D'Ambrosio et al.
11,850,073 B2 12/2023 Wright et al.
11,850,414 B2 12/2023 Schenck et al.
11,850,415 B2 12/2023 Schwammenthal et al.
D1,012,284 S 1/2024 Glaser et al.
11,857,345 B2 1/2024 Hanson et al.
11,864,878 B2 1/2024 Duval et al.
11,872,384 B2 1/2024 Cotter
11,883,207 B2 1/2024 El Katerji et al.
D1,014,552 S 2/2024 Lussier et al.
11,890,082 B2 2/2024 Cros et al.
11,896,199 B2 2/2024 Lent et al.
11,900,660 B2 2/2024 Saito et al.
11,903,657 B2 2/2024 Geric et al.
11,906,411 B2 2/2024 Graichen et al.
11,911,550 B2 2/2024 Itamochi et al.
D1,017,634 S 3/2024 Lussier et al.
D1,017,699 S 3/2024 Moore et al.
11,923,078 B2 3/2024 Fallen et al.
11,923,093 B2 3/2024 Moffitt et al.
11,925,794 B2 3/2024 Malkin et al.
11,931,073 B2 3/2024 Walsh et al.
11,931,528 B2 3/2024 Rohl et al.
11,931,588 B2 3/2024 Aghassian
11,986,274 B2 5/2024 Edelman
12,017,076 B2 6/2024 Tan et al.
12,023,476 B2 7/2024 Tuval et al.
12,029,891 B2 7/2024 Siess et al.
12,059,559 B2 8/2024 Muller et al.
D1,043,730 S 9/2024 Lussier et al.
D1,043,731 S 9/2024 Lussier et al.
12,076,544 B2 9/2024 Siess et al.
12,097,016 B2 9/2024 Goldvasser
12,102,815 B2 10/2024 Dhaliwal et al.
12,144,650 B2 11/2024 Spanier et al.
12,144,976 B2 11/2024 Baumbach et al.
12,178,554 B2 12/2024 Stotz et al.
12,179,009 B2 12/2024 El Katerji et al.
12,183,459 B2 12/2024 Agnello et al.
12,194,287 B2 1/2025 Kassel et al.
12,201,821 B2 1/2025 Schlebusch et al.
12,211,615 B2 1/2025 Nix et al.
D1,060,379 S 2/2025 Lussier et al.
12,213,771 B2 2/2025 Curran et al.
12,217,850 B2 2/2025 Agnello
12,222,267 B2 2/2025 Stotz et al.
12,251,551 B2 3/2025 Liu et al.
12,257,424 B2 3/2025 Schlebusch et al.
12,268,861 B2 4/2025 D'Ambrosio et al.
12,296,158 B2 5/2025 Higgins et al.
12,296,159 B2 5/2025 Schilling et al.
12,310,621 B2 5/2025 Murphy
12,310,708 B2 5/2025 Schlebusch et al.
12,311,160 B2 5/2025 Schlebusch et al.
12,324,906 B2 6/2025 Baumbach et al.

(56) References Cited

U.S. PATENT DOCUMENTS 12,329,501 B2 6/2025 Moyer et al.
12,329,956 B2 6/2025 Sunagawa
12,329,959 B2 6/2025 Hassan et al.
12,343,518 B2 7/2025 Tuval et al.
D1,090,610 S 8/2025 Kroeker et al.
12,377,256 B2 8/2025 Stotz et al.
12,390,168 B2 8/2025 Katerji et al.
12,397,099 B2 8/2025 Germain et al.
D1,092,492 S 9/2025 Lussier et al.
12,409,313 B2 9/2025 Eggen et al.
2001/0016686 A1 8/2001 Okada et al.
2001/0037093 A1 11/2001 Benkowski et al.
2001/0039828 A1 11/2001 Shin et al.
2002/0022785 A1 2/2002 Romano
2002/0082585 A1 6/2002 Carroll et al.
2002/0093412 A1 7/2002 Morrison
2002/0147495 A1 10/2002 Petroff
2002/0151761 A1 10/2002 Viole et al.
2003/0069465 A1 4/2003 Benkowski et al.
2003/0130581 A1 7/2003 Salo et al.
2003/0139643 A1 7/2003 Smith et al.
2003/0167002 A1 9/2003 Nagar et al.
2003/0191357 A1 10/2003 Frazier
2003/0199727 A1 10/2003 Burke
2004/0022640 A1 2/2004 Siess et al.
2004/0044266 A1 3/2004 Siess et al.
2004/0065143 A1 4/2004 Husher
2004/0124979 A1 7/2004 Medema
2004/0130009 A1 7/2004 Tangpuz
2004/0167376 A1 8/2004 Peters et al.
2004/0167410 A1 8/2004 Hettrick
2004/0225177 A1 11/2004 Coleman et al.
2004/0241019 A1 12/2004 Goldowsky
2004/0260346 A1 12/2004 Overall et al.
2005/0001324 A1 1/2005 Dunr
2005/0019167 A1 1/2005 Nusser et al.
2005/0107658 A1 5/2005 Brockway
2005/0126268 A1 6/2005 Ouriev et al.
2005/0267322 A1 12/2005 LaRose
2006/0030809 A1 2/2006 Barzilay et al.
2006/0108697 A1 5/2006 Wang
2006/0108901 A1 5/2006 Mao-Chin
2006/0122583 A1 6/2006 Pesach et al.
2006/0196277 A1 9/2006 Allen et al.
2006/0229488 A1 10/2006 Ayre et al.
2006/0287600 A1 12/2006 McEowen
2006/0287604 A1 12/2006 Hickey
2007/0060787 A1 3/2007 Peters et al.
2007/0069354 A1 3/2007 Dangelmaier
2007/0073352 A1 3/2007 Euler et al.
2007/0088214 A1* 4/2007 Shuros ................. A61B 8/4483 600/437
2007/0156006 A1 7/2007 Smith et al.
2007/0255352 A1 11/2007 Roline et al.
2007/0266778 A1 11/2007 Corey et al.
2007/0282209 A1 12/2007 Lui et al.
2007/0299325 A1 12/2007 Farrell et al.
2008/0015517 A1 1/2008 Geistert et al.
2008/0082005 A1 4/2008 Stern et al.
2008/0091239 A1 4/2008 Johansson et al.
2008/0097595 A1 4/2008 Gabbay
2008/0102096 A1 5/2008 Molin et al.
2008/0108901 A1 5/2008 Baba et al.
2008/0108930 A1 5/2008 Weitzel et al.
2008/0133006 A1* 6/2008 Crosby ............... A61M 60/876 623/3.13
2008/0146996 A1 6/2008 Smisson
2008/0210016 A1 9/2008 Zwirn et al.
2008/0248614 A1 10/2008 Yang
2008/0262289 A1 10/2008 Goldowsky
2008/0262361 A1 10/2008 Gutfinger et al.
2008/0269822 A1 10/2008 Ljungstrom et al.
2008/0275339 A1 11/2008 Thiemann et al.
2008/0287799 A1* 11/2008 Hall ......................... A61B 8/13 600/454
2008/0306328 A1 12/2008 Ercolani
2009/0024042 A1 1/2009 Nunez et al.
2009/0025459 A1 1/2009 Zhang et al.
2009/0064755 A1 3/2009 Fleischli et al.
2009/0105799 A1 4/2009 Hekmat et al.
2009/0131765 A1 5/2009 Roschak et al.
2009/0204163 A1 8/2009 Shuros et al.
2009/0226328 A1 9/2009 Morello
2009/0312650 A1 12/2009 Maile et al.
2010/0010354 A1 1/2010 Skerl et al.
2010/0082099 A1 4/2010 Vodermayer et al.
2010/0087742 A1 4/2010 Bishop et al.
2010/0160801 A1 6/2010 Takatani et al.
2010/0219967 A1 9/2010 Kaufmann
2010/0222632 A1 9/2010 Poirier
2010/0222633 A1 9/2010 Poirier
2010/0222635 A1 9/2010 Poirier
2010/0222878 A1 9/2010 Poirier
2010/0268017 A1 10/2010 Siess
2010/0298625 A1 11/2010 Reichenbach et al.
2010/0324378 A1 12/2010 Tran et al.
2011/0004075 A1 1/2011 Stahmann et al.
2011/0022057 A1 1/2011 Eigler et al.
2011/0071336 A1 3/2011 Yomtov
2011/0144744 A1 6/2011 Wampler
2011/0160516 A1 6/2011 Dague
2011/0172505 A1 7/2011 Kim
2011/0184301 A1 7/2011 Holmstrom
2011/0186943 A1 8/2011 Pahl
2011/0218435 A1 9/2011 Srinivasan et al.
2011/0230068 A1 9/2011 Pahl
2012/0022645 A1 1/2012 Burke
2012/0029408 A1 2/2012 Beaudin
2012/0084024 A1 4/2012 Norcross, Jr.
2012/0150089 A1 6/2012 Penka et al.
2012/0150291 A1 6/2012 Aber
2012/0197141 A1 8/2012 Vanney
2012/0203476 A1 8/2012 Dam
2012/0245404 A1 9/2012 Smith
2012/0247200 A1 10/2012 Ahonen et al.
2012/0310037 A1 12/2012 Choi et al.
2012/0330214 A1 12/2012 Peters et al.
2013/0041204 A1 2/2013 Heilman et al.
2013/0046129 A1 2/2013 Medvedev et al.
2013/0066141 A1 3/2013 Doerr et al.
2013/0066142 A1 3/2013 Doerr et al.
2013/0072846 A1 3/2013 Heide et al.
2013/0116575 A1 5/2013 Mickle et al.
2013/0144379 A1 6/2013 Najafi et al.
2013/0289334 A1 10/2013 Badstibner
2013/0289376 A1 10/2013 Lang
2013/0303831 A1 11/2013 Evans
2013/0304404 A1 11/2013 Dam
2014/0005467 A1 1/2014 Farnan et al.
2014/0013852 A1 1/2014 Brown et al.
2014/0030122 A1 1/2014 Ozaki
2014/0100414 A1 4/2014 Tamez et al.
2014/0114202 A1 4/2014 Hein et al.
2014/0128659 A1 5/2014 Heuring et al.
2014/0200389 A1 7/2014 Yanai et al.
2014/0243688 A1 8/2014 Caron et al.
2014/0275720 A1 9/2014 Ferrari
2014/0275727 A1 9/2014 Bonde
2014/0296677 A1 10/2014 McEowen
2014/0303426 A1 10/2014 Kerkhoffs et al.
2014/0342203 A1 11/2014 Elian
2015/0032007 A1 1/2015 Ottevanger et al.
2015/0080743 A1 3/2015 Siess
2015/0141832 A1 5/2015 Yu et al.
2015/0141842 A1 5/2015 Spanier et al.
2015/0157216 A1 6/2015 Stigall et al.
2015/0174307 A1 6/2015 Eckman et al.
2015/0190092 A1 7/2015 Mori
2015/0196076 A1 7/2015 Billingslea
2015/0201900 A1* 7/2015 Syed ......................... A61F 2/95 600/424
2015/0250935 A1 9/2015 Anderson et al.
2015/0273184 A1 10/2015 Scott et al.
2015/0290372 A1 10/2015 Muller et al.

(56) References Cited

U.S. PATENT DOCUMENTS

2015/0306290 A1 10/2015 Rosenberg et al.
2015/0306291 A1 10/2015 Bonde et al.
2015/0307344 A1 10/2015 Ernst
2015/0327921 A1 11/2015 Govari
2015/0335804 A1 11/2015 Marseille et al.
2015/0365738 A1 12/2015 Purvis et al.
2016/0000983 A1 1/2016 Mohl et al.
2016/0008531 A1 1/2016 Wang et al.
2016/0022889 A1 1/2016 Bluvshtein et al.
2016/0022890 A1 1/2016 Schwammenthal et al.
2016/0045165 A1 2/2016 Braido et al.
2016/0095968 A1 4/2016 Rudser
2016/0101230 A1 4/2016 Ochsner et al.
2016/0144166 A1 5/2016 Decré et al.
2016/0151553 A1 6/2016 Bonde
2016/0166747 A1 6/2016 Frazier et al.
2016/0213828 A1 7/2016 Sievers
2016/0250399 A1 9/2016 Tiller et al.
2016/0278856 A1 9/2016 Panescu
2016/0302672 A1 10/2016 Kuri
2016/0303299 A1 10/2016 Muller
2016/0317043 A1 11/2016 Campo
2016/0338629 A1 11/2016 Doerr
2017/0010144 A1 1/2017 Lenner et al.
2017/0021070 A1 1/2017 Petersen
2017/0049945 A1 2/2017 Halvorsen et al.
2017/0086780 A1 3/2017 Sokulin et al.
2017/0098491 A1 4/2017 Ziaie et al.
2017/0112985 A1 4/2017 Yomtov
2017/0128646 A1 5/2017 Karch
2017/0136164 A1 5/2017 Yeatts
2017/0202575 A1 7/2017 Stanfield et al.
2017/0224279 A1 8/2017 Cahan et al.
2017/0239407 A1 8/2017 Hayward
2017/0258980 A1 9/2017 Katsuki et al.
2017/0348470 A1 12/2017 D'Ambrosio et al.
2017/0354812 A1 12/2017 Callaghan et al.
2018/0064860 A1 3/2018 Nunez et al.
2018/0078159 A1 3/2018 Edelman et al.
2018/0093070 A1 4/2018 Cottone
2018/0110910 A1 4/2018 Rodemerk et al.
2018/0126053 A1 5/2018 Zilbershlag et al.
2018/0199635 A1 7/2018 Longinotti-Buitoni et al.
2018/0250457 A1 9/2018 Morello et al.
2018/0256796 A1 9/2018 Hansen
2018/0256800 A1 9/2018 Conyers et al.
2018/0264182 A1 9/2018 Spanier et al.
2018/0280598 A1 10/2018 Curran et al.
2018/0316209 A1 11/2018 Gliner
2018/0326131 A1 11/2018 Muller et al.
2018/0333059 A1 11/2018 Casas
2018/0353667 A1 12/2018 Moyer et al.
2018/0369469 A1 12/2018 Le Duc De Lillers et al.
2019/0001038 A1 1/2019 Yomtov et al.
2019/0054223 A1 2/2019 Frazier et al.
2019/0083690 A1 3/2019 Siess et al.
2019/0192752 A1 6/2019 Tiller et al.
2019/0192753 A1 6/2019 Liu et al.
2019/0209755 A1 7/2019 Nix et al.
2019/0209758 A1 7/2019 Tuval et al.
2019/0216995 A1 7/2019 Kapur et al.
2019/0217002 A1 7/2019 Urakabe
2019/0223877 A1 7/2019 Nitzen et al.
2019/0240680 A1 8/2019 Hayakawa
2019/0254543 A1 8/2019 Hartholt et al.
2019/0282741 A1 9/2019 Franano et al.
2019/0282744 A1 9/2019 D'Ambrosio et al.
2019/0351117 A1 11/2019 Cambronne et al.
2019/0351118 A1 11/2019 Graichen et al.
2020/0016309 A1 1/2020 Kallenbach et al.
2020/0028376 A1 1/2020 Ha
2020/0038567 A1 2/2020 Siess et al.
2020/0060559 A1 2/2020 Edelman et al.
2020/0069857 A1 3/2020 Schwammenthal et al.
2020/0147283 A1 5/2020 Tanner et al.
2020/0164125 A1 5/2020 Muller et al.
2020/0164126 A1 5/2020 Muller
2020/0253583 A1 8/2020 Brisken et al.
2020/0312450 A1 10/2020 Agnello et al.
2021/0268264 A1 9/2021 Stotz
2021/0290087 A1 9/2021 Schlebusch
2021/0290930 A1 9/2021 Kasel
2021/0290933 A1 9/2021 Stotz
2021/0339002 A1 11/2021 Schlebusch et al.
2021/0339004 A1 11/2021 Schlebusch et al.
2021/0346674 A1 11/2021 Baumbach et al.
2021/0346675 A1 11/2021 Schlebusch et al.
2021/0346676 A1 11/2021 Schlebusch et al.
2021/0346677 A1 11/2021 Baumbach et al.
2021/0346678 A1 11/2021 Baumbach et al.
2021/0378523 A1 12/2021 Budde
2021/0379359 A1 12/2021 Schellenberg
2021/0379360 A1 12/2021 Schellenberg
2021/0393944 A1 12/2021 Wenning
2022/0016411 A1 1/2022 Winterwerber
2022/0032036 A1 2/2022 Baumbach et al.
2022/0039669 A1 2/2022 Schlebusch et al.
2022/0047173 A1 2/2022 Stotz et al.
2022/0050037 A1 2/2022 Stotz et al.
2022/0072298 A1 3/2022 Spanier et al.
2022/0076807 A1 3/2022 Agnello
2022/0079457 A1 3/2022 Tuval et al.
2022/0105339 A1 4/2022 Nix et al.
2022/0126085 A1 4/2022 Farnan
2022/0126086 A1 4/2022 Schlebusch et al.
2022/0142462 A1 5/2022 Douk et al.
2022/0161019 A1 5/2022 Mitze et al.
2022/0361762 A1 11/2022 Lalancette
2023/0173250 A1 6/2023 Stigloher
2023/0191141 A1 6/2023 Wenning et al.
2024/0011808 A1 1/2024 Winzer et al.
2024/0074828 A1 3/2024 Wenning
2024/0245902 A1 7/2024 Schlebusch et al.
2025/0032773 A1 1/2025 Baumbach et al.
2025/0121177 A1 4/2025 West
2025/0143587 A1 5/2025 Stotz
2025/0144397 A1 5/2025 Kassel et al.
2025/0222247 A1 7/2025 Schlebusch
2025/0235687 A1 7/2025 Schlebusch et al.
2025/0251330 A1 8/2025 Stotz
2025/0281060 A1 9/2025 Schlebusch et al.

FOREIGN PATENT DOCUMENTS

CN 1222862 A 7/1999
CN 1202871 C 5/2005
CN 1661338 A 8/2005
CN 101128168 2/2008
CN 101208045 6/2008
CN 101214158 7/2008
CN 101351237 1/2009
CN 101448535 6/2009
CN 101460094 6/2009
CN 101579233 11/2009
CN 201437016 4/2010
CN 101711683 5/2010
CN 201658687 12/2010
CN 102421372 4/2012
CN 102803923 11/2012
CN 103328018 9/2013
CN 103857326 6/2014
CN 103957957 7/2014
CN 104105449 10/2014
CN 104188687 12/2014
CN 106104229 11/2016
CN 106333707 1/2017
CN 206007680 3/2017
CN 107530479 1/2018
CN 107632167 1/2018
CN 109939282 6/2019
CN 209790495 12/2019
CN 210020563 2/2020
CN 215841206 2/2022
CN 217828630 11/2022

(56) References Cited

FOREIGN PATENT DOCUMENTS

| | | |
|---|---|---|
| CN | 219250364 | 6/2023 |
| CN | 118320294 | 7/2024 |
| CN | 113769260 | 9/2024 |
| CN | 118920928 | 11/2024 |
| DE | 195 20 920 | 12/1995 |
| DE | 198 21 307 | 10/1999 |
| DE | 100 59 714 | 5/2002 |
| DE | 100 60 275 | 6/2002 |
| DE | 101 44 269 | 3/2003 |
| DE | 102 26 305 | 10/2003 |
| DE | 10 2006 001 180 | 9/2007 |
| DE | 10 2009 007 216 | 8/2010 |
| DE | 10 2009 011 726 | 9/2010 |
| DE | 10 2009 025 464 | 1/2011 |
| DE | 10 2009 047 845 | 3/2011 |
| DE | 10 2011 106 142 | 12/2012 |
| DE | 20 2011 110 389 | 9/2013 |
| DE | 10 2015 004 177 | 10/2015 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2018 208 536 | 12/2019 |
| DE | 10 2018 208 862 | 12/2019 |
| DE | 10 2018 208 916 | 12/2019 |
| DE | 10 2018 208 927 | 12/2019 |
| DE | 10 2018 208 945 | 12/2019 |
| DE | 10 2018 210 076 | 12/2019 |
| DE | 10 2018 212 153 | 1/2020 |
| DE | 10 2018 213 151 | 2/2020 |
| DE | 10 2018 213 350 | 2/2020 |
| DE | 10 2018 220 658 | 6/2020 |
| DE | 10 2018 222 505 | 6/2020 |
| DE | 10 2020 102 473 | 8/2021 |
| DE | 11 2020 003 151 | 3/2022 |
| EP | 0 794 411 | 9/1997 |
| EP | 0 916 359 | 5/1999 |
| EP | 1 062 959 | 12/2000 |
| EP | 1 339 443 | 11/2001 |
| EP | 1 011 803 | 9/2004 |
| EP | 1 354 606 | 6/2006 |
| EP | 2 143 385 | 1/2010 |
| EP | 2 175 770 | 4/2010 |
| EP | 2 187 807 | 6/2012 |
| EP | 2 570 143 | 3/2013 |
| EP | 2 401 003 | 10/2013 |
| EP | 1 871 441 | 11/2014 |
| EP | 2 859 911 | 4/2015 |
| EP | 2 213 227 | 8/2016 |
| EP | 2 835 141 | 8/2016 |
| EP | 3 088 016 | 11/2016 |
| EP | 2 585 129 | 3/2017 |
| EP | 2 945 661 | 11/2017 |
| EP | 2 136 861 | 12/2017 |
| EP | 3 020 426 | 12/2017 |
| EP | 3 287 154 | 2/2018 |
| EP | 3 205 359 | 8/2018 |
| EP | 3 205 360 | 8/2018 |
| EP | 3 378 421 | 9/2018 |
| EP | 3 389 738 | 8/2019 |
| EP | 2 505 090 | 12/2019 |
| EP | 3 668 560 | 6/2020 |
| EP | 3 720 520 | 10/2020 |
| EP | 3 753 594 | 12/2020 |
| EP | 3 357 523 | 1/2021 |
| EP | 3 490 628 | 2/2021 |
| EP | 3 487 548 | 3/2021 |
| EP | 3 509 661 | 3/2021 |
| EP | 3 515 523 | 3/2021 |
| EP | 3 528 863 | 3/2021 |
| EP | 3 615 103 | 3/2021 |
| EP | 4 271 461 | 3/2021 |
| EP | 3 131 600 | 6/2021 |
| EP | 3 131 615 | 6/2021 |
| EP | 3 463 505 | 9/2021 |
| EP | 3 884 970 | 9/2021 |
| EP | 2 599 510 | 10/2021 |
| EP | 3 003 421 | 10/2021 |
| EP | 3 027 241 | 10/2021 |
| EP | 3 668 561 | 10/2021 |
| EP | 3 164 168 | 12/2021 |
| EP | 3 344 129 | 12/2021 |
| EP | 3 624 867 | 3/2022 |
| EP | 3 651 822 | 3/2022 |
| EP | 3 689 389 | 3/2022 |
| EP | 3 737 436 | 3/2022 |
| EP | 3 972 661 | 3/2022 |
| EP | 3 984 589 | 4/2022 |
| EP | 3 654 006 | 5/2022 |
| EP | 3 737 310 | 7/2022 |
| EP | 2 999 400 | 8/2022 |
| EP | 3 711 788 | 8/2022 |
| EP | 3 694 573 | 9/2022 |
| EP | 3 600 477 | 10/2022 |
| EP | 3 897 768 | 10/2022 |
| EP | 2 892 583 | 1/2023 |
| EP | 3 370 797 | 1/2023 |
| EP | 3 597 231 | 1/2023 |
| EP | 3 668 562 | 1/2023 |
| EP | 3 856 275 | 1/2023 |
| EP | 3 003 420 | 2/2023 |
| EP | 3 397 299 | 2/2023 |
| EP | 3 046 594 | 3/2023 |
| EP | 3 938 005 | 4/2023 |
| EP | 3 685 562 | 5/2023 |
| EP | 3 397 298 | 7/2023 |
| EP | 3 809 959 | 7/2023 |
| EP | 2 072 150 | 9/2023 |
| EP | 2 961 984 | 9/2023 |
| EP | 3 352 808 | 9/2023 |
| EP | 3 768 156 | 9/2023 |
| EP | 4 052 754 | 10/2023 |
| EP | 3 157 596 | 11/2023 |
| EP | 3 766 428 | 11/2023 |
| EP | 3 781 027 | 11/2023 |
| EP | 4 061 470 | 11/2023 |
| EP | 4 070 720 | 11/2023 |
| EP | 3 449 958 | 12/2023 |
| EP | 3 687 596 | 12/2023 |
| EP | 3 768 340 | 12/2023 |
| EP | 3 801 675 | 1/2024 |
| EP | 3 566 636 | 2/2024 |
| EP | 3 634 526 | 2/2024 |
| EP | 3 768 347 | 2/2024 |
| EP | 3 790 606 | 2/2024 |
| EP | 3 930 780 | 2/2024 |
| EP | 3 397 147 | 3/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 970 765 | 7/2024 |
| EP | 3 854 444 | 9/2024 |
| EP | 3 793 674 | 10/2024 |
| EP | 3 618 885 | 11/2024 |
| EP | 4 034 221 | 11/2024 |
| EP | 3 809 960 | 12/2024 |
| EP | 3 854 446 | 2/2025 |
| EP | 4 429 754 | 2/2025 |
| EP | 3 970 785 | 3/2025 |
| EP | 4 429 753 | 3/2025 |
| EP | 3 950 043 | 5/2025 |
| EP | 3 899 964 | 6/2025 |
| EP | 3 948 888 | 6/2025 |
| EP | 3 965 845 | 6/2025 |
| EP | 4 039 319 | 6/2025 |
| EP | 4 297 672 | 7/2025 |
| EP | 3 668 559 | 8/2025 |
| EP | 3 848 088 | 8/2025 |
| EP | 4 218 556 | 9/2025 |
| ES | 2 913 485 | 6/2022 |
| JP | S59-080229 | 5/1984 |
| JP | S61-125329 | 6/1986 |

(56) References Cited

FOREIGN PATENT DOCUMENTS

| | | |
|---|---|---|
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | H02-234750 | 9/1990 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2005-028137 | 2/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-518907 | 6/2010 |
| JP | 2012-520157 | 9/2012 |
| JP | 2013-128792 | 7/2013 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2017-500932 | 1/2017 |
| JP | 2017-176719 | 10/2017 |
| JP | 2017-532084 | 11/2017 |
| JP | 2019-523110 | 8/2019 |
| JP | 2020-072985 | 5/2020 |
| WO | WO 89/006513 | 1/1989 |
| WO | WO 92/015239 | 9/1992 |
| WO | WO 94/009835 | 5/1994 |
| WO | WO 98/043688 | 10/1998 |
| WO | WO 00/033047 | 6/2000 |
| WO | WO 2006/122001 | 11/2006 |
| WO | WO 2010/142286 | 12/2010 |
| WO | WO 2010/143272 | 12/2010 |
| WO | WO 2012/018917 | 2/2012 |
| WO | WO 2012/112378 | 8/2012 |
| WO | WO 2013/160443 | 10/2013 |
| WO | WO 2014/042925 | 3/2014 |
| WO | WO 2014/141284 | 9/2014 |
| WO | WO 2014/165635 | 10/2014 |
| WO | WO 2015/085220 | 6/2015 |
| WO | WO 2016/001284 | 1/2016 |
| WO | WO 2016/066180 | 5/2016 |
| WO | WO 2016/137743 | 9/2016 |
| WO | WO 2017/032751 | 3/2017 |
| WO | WO 2017/066257 | 4/2017 |
| WO | WO 2017/106190 | 6/2017 |
| WO | WO 2017/147291 | 8/2017 |
| WO | WO 2017/214118 | 12/2017 |
| WO | WO 2018/005228 | 1/2018 |
| WO | WO 2018/048800 | 3/2018 |
| WO | WO 2018/109038 | 6/2018 |
| WO | WO 2018/213089 | 11/2018 |
| WO | WO 2019/013794 | 1/2019 |
| WO | WO 2019/034670 | 2/2019 |
| WO | WO 2019/034775 | 2/2019 |
| WO | WO 2019/078723 | 4/2019 |
| WO | WO 2019/126721 | 6/2019 |
| WO | WO 2019/137911 | 7/2019 |
| WO | WO 2019/193604 | 10/2019 |
| WO | WO 2019/219883 | 11/2019 |
| WO | WO 2019/229210 | 12/2019 |
| WO | WO 2019/229220 | 12/2019 |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/243582 | 12/2019 |
| WO | WO 2020/030686 | 2/2020 |
| WO | WO 2020/030706 | 2/2020 |
| WO | WO 2020/064707 | 4/2020 |
| WO | WO 2020/089429 | 5/2020 |
| WO | WO 2020/198280 | 10/2020 |
| WO | WO 2020/243756 | 12/2020 |
| WO | WO 2023/040546 | 12/2021 |
| WO | WO 2022/074136 | 4/2022 |
| WO | WO 2022/109590 | 5/2022 |
| WO | WO 2022/173970 | 8/2022 |
| WO | WO 2023/226779 | 9/2022 |
| WO | WO 2023/049813 | 3/2023 |
| WO | WO 2024/104184 | 5/2024 |

OTHER PUBLICATIONS

International Preliminary Report on Patentability and Written Opinion received in PCT Application No. PCT/EP2019/071204, dated Feb. 18, 2021 in 17 pages.

International Search Report and Written Opinion received in PCT Application No. PCT/EP2019/071204, dated Nov. 7, 2019 in 23 pages.

Kong et al., "A Stein Equation Approach for Solutions to the Diophantine Equations," 2010 Chinese Control and Decision Conference, Xuzhou, May 26, 2010, pp. 3024-3028.

Koseli et al., "Online Viscosity Measurement of Complex Solutions Using Ultrasound Doppler Velocimetry", Turk J Chem, Jan. 2006, vol. 30, pp. 297-305.

McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.

Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.

Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.

Atkinson et al., "Pulse-Doppler Ultrasound and Its Clinical Application", The Yale Journal of Biology and Medicine, 1977, vol. 50, pp. 367-373.

Leguy et al., "Assessment of Blood vol. Flow in Slightly Curved Arteries from a Single Velocity Profile", Journal of Biomechanics, 2009, pp. 1664-1672.

Lombardi et al., "Flow Rate Profiler: an instrument to measure blood velocity profiles", Ultrasonics, 2001, vol. 39, pp. 143-150.

Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.

(56) References Cited

OTHER PUBLICATIONS

Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.
"Understanding Hot-Wire Anemometry", Advanced Thermal Solutions, Inc., 2007, pp. 13-17.
Vieli, A., "Doppler Flow Determination", BJA: British Journal of Anaesthesia, 1988, vol. 60, pp. 107S-112S.
Vollkron et al., "Advanced Suction Detection for an Axial Flow Pump", Artificial Organs, 2006, vol. 30, No. 9, pp. 665-670.
Vollkron et al., "Development of a Suction Detection System for Axial Blood Pumps", Artificial Organs, 2004, vol. 28, No. 8, pp. 709-716.
Yuanyuan et al., "Characteristics Analysis for Doppler Ultrasound Blood Flow Signals", China Medical Device Information, 5(1), Feb. 28, 1999, pp. 36-42.
Zhang, Dabiao et al., "Design of Microwave Velocity and Distance Monitor System", Instrument Technique and Sensor, Hebei Normal University, Apr. 25, 2004, pp. 3.
HeartMate 3™ Left Ventricular Assist System, Instructions for Use, Thoratec Corporation, Aug. 2017, pp. 536. [Uploaded in 3 parts].
Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.
Chung et al., "Improved Efficiency Characteristics of Wireless Power Charging System for Superconducting MAGLEV Train Using Inserted Permanent Magnets," 2018 IEEE International Symposium on Electromagnetic Compatibility, 2018, pp. 564-567.
"ECG Electrodes product comparison chart," 3M.com, 2018, https://multimedia.3m.com/mws/media/14908830/red-dot-ecg-electrodes-comparison-chart.pdf, accessed May 18, 2025, 1 page.
Eeckhout, MD, PhD, et al., "Handbook of Complications During Percutaneous Cardiovascular Interventions", 2007 Informa UK Ltd., Ch. 12, pp. 167-177.
Mack-Haynes, Robin, "Fasteners Made Easy," New Mexico State University, https://pubs.nmsu.edu/_c/C232.pdf, accessed May 18, 2025, pp. 8.
Mullins, Charles E., MD, "Cardiac Catheterization in Congenital Heart Disease: Pediatric and Adult", Blackwell Futura, 2006, Chapters 3, 4 and 32, pp. 101.
Radiologyinfo.org, "Subcutaneous Port," Definition, https://www.radiologyinfo.org/en/glossary?id=ezNFREEzNEFFLTI5OTAtNDVFNy04MkVBLTA1RDVGMDdBMzNFRH0=&i=1&b=0&modal=1, accessed Sep. 2, 2025, 1 page.
Sigg et al., "Cardiac Electophysiology Methods and Models", Springer, Clinical Perspective: Electrophysiology in the Young and Patients with Congenital Heart Disease, Ch. 23, 2010, pp. 457-477.
Walser, Eric, "Venous access ports: indications, implantation technique, follow-up, and complications;" Cardiovasc Intervent Radial, Aug. 2012; vol. 35, No. 4, pp. 751-764. (Abstract Only).
Tan et al., "Surface Engineering and Patterning Using Parlene for Biological Applications." Materials (Basel), Mar. 15, 2010, vol. 3, No. 3, pp. 1803-1832.

* cited by examiner

IMPLANTABLE CARDIAC SUPPORT SYSTEM

BACKGROUND

Field

The invention relates to an implantable vascular support system and a method for determining a total fluid volume flow in the region of an implanted vascular support system. The invention can in particular be used in (fully) implanted left ventricular assist devices (LVAD).

Description of the Related Art

Implanted left ventricular assist devices (LVAD) exist primarily in two design variants. The first are (percutaneous) minimally-invasive left ventricular assist devices. The second variant are left ventricular assist devices which are invasively implanted under an opening in the rib cage. The first variant conveys blood directly from the left ventricle into the aorta, because the (percutaneous) minimally invasive left ventricular assist device is positioned centrally in the aortic valve. The second variant conveys the blood from the left ventricle into the aorta via a bypass tube.

The task of a cardiac support system is to convey blood. The so-called cardiac output (CO, usually expressed in liters per minute) is of high clinical relevance here. Simply put, the cardiac output refers to the total volume flow of blood (out of a ventricle), in particular from the left ventricle to the aorta. The initial objective is therefore to obtain this parameter as a measured value during the operation of a cardiac support system.

Depending on the level of support, which describes the proportion of volume flow conveyed by a conveying means, such as a pump of the support system, to the total volume flow of blood from the ventricle to the aorta, a specific amount of volume flow reaches the aorta via the physiological path through the aortic valve. The cardiac output or the total volume flow ($Q_{CO}$) from the ventricle to the aorta is therefore usually the sum of the pump volume flow ($Q_p$) and the aortic valve volume flow ($Q_a$).

In the clinical setting, the use of dilution methods is an established procedure for determining the cardiac output ($Q_{CO}$). However, these dilutions methods all rely on a transcutaneously inserted catheter and can therefore only provide cardiac output measurement data during cardiac surgery. Whereas the determination of the cardiac output by a support system is difficult to implement, the pump volume flow ($Q_p$) can be determined by means of suitable components of the support system. For high levels of support ($Q_p/Q_{CO}$), the aortic valve volume flow ($Q_a$) approaches zero or becomes negligibly small, so that $Q_p$ approximately equals CO or the pump volume flow ($Q_p$) can be used as an approximation for the cardiac output ($Q_{CO}$).

Correlating the operating parameters of the support system, particularly the electrical power consumption, possibly supplemented by other physiological parameters, such as the blood pressure, is an established procedure for measuring the pump volume flow ($Q_p$).

SUMMARY

The integration of dedicated ultrasound measurement technology into a cardiac support system has also already been demonstrated. It should be noted here, that the known ultrasound measurement technology can only measure the pump volume flow and cannot take into account a bypass flow through the aortic valves past the support system.

Based on this, the underlying object of the invention is to further improve the systems and methods known in the state of the art and to enable the most accurate possible determination of measurement parameters such as a fluid flow, in particular the cardiac output, by the support system itself, even at normal or low levels of support.

Systems and methods disclosed herein propose an implantable vascular support system having a cannula and an ultrasound measuring device, wherein the cannula and the ultrasound measuring device are provided in the region of oppositely disposed ends of the support system.

The solution proposed here advantageously allows the cardiac output or the total fluid volume flow out of a ventricle to be determined by the support system itself with the aid of ultrasound measurement technology integrated in or on the support system.

In other words, the solution proposed here in particular describes a system and/or a method for determining the total cardiac output (CO) of a patient with an implanted left ventricular cardiac support system (LVAD). The CO is one of the most important parameters for the support of human circulation by an LVAD, so making this parameter continuously available during operation, in particular as a control parameter, is desirable. The solution proposed here is based in particular on the integration of one or more ultrasound transducers into the proximal end of an LVAD. In this context, proximal means in particular that this end is located in the region of the aorta. The CO can in particular be determined by combining at least two Doppler velocity measurements and at least one distance measurement (by considering the signal transit time, see time of flight).

The vascular support system is preferably a cardiac support system, particularly preferably a ventricular support system. The support system is routinely used to support the conveyance of blood in the circulatory system of a human being, if applicable a patient. The support system can be disposed at least partially in a blood vessel. The blood vessel is the aorta, for example, in particular in the case of a left ventricular assist device, or the common trunk (truncus pulmonalis) into the two pulmonary arteries, in particular in the case of a right ventricular assist device. The support system is preferably disposed at the outlet of the left ventricle of the heart or the left ventricle. The support system is particularly preferably disposed in aortic valve position.

The support system is preferably a left ventricular cardiac support system (LVAD) or a percutaneous, minimally invasive left ventricular assist device. The support system is particularly preferably configured and/or suited to being disposed at least partially in a ventricle, preferably in the left ventricle of a heart, and/or in an aorta, in particular in aortic valve position.

The support system is furthermore preferably fully implantable. In other words, this means in particular that the means required for determination, in particular the ultrasound transducers, are located entirely inside the body of the patient and remain there. The cannula and the ultrasound measuring device of the support system are preferably configured to be accommodated entirely inside the body of the patient and to remain there. The support system can also have a multipart design, i.e. comprise a plurality of components that can be disposed spaced apart from one another, so that the ultrasound transducers and the control device (processing unit/measuring unit), for example, can be disposed separated from one another by a wire. In the multipart design, the control device disposed separate from the ultrasound measuring device can likewise be implanted or it can be disposed outside the patient's body. Either way, it is not absolutely necessary for a control device and/or a processing unit to also be disposed in the body of the patient. For example, the support system can be implanted such that a control device and/or a processing unit (the support system) is disposed on the patient's skin or outside the patient's body and a connection to the sensor system disposed in the body is established.

Fully implanted in this context means in particular that the means required for determination (here the ultrasound sensor system) are located entirely inside the patient's body and remain there. This advantageously enables the cardiac output to be determined even outside of cardiac surgery.

The cannula can be a so-called inlet cannula. The support system furthermore preferably comprises a flow machine, such as a pump and/or an electric motor. The electric motor is a routine component of the flow machine. The (inlet) cannula is preferably configured such that, in the implanted state, it can guide fluid from a (left) ventricle of a heart to the flow machine. The support system is preferably elongated and/or hose-like. The cannula and the flow machine are preferably provided in the region of oppositely disposed ends of the support system. The cannula usually forms or surrounds a fluid channel. The fluid channel usually extends between the inlet opening and the discharge opening of the support system. The inlet opening and the discharge opening are routinely also provided in the region of oppositely disposed ends of the support system.

The cannula and the ultrasound measuring device are provided in the region of oppositely disposed ends of the (elongated/hose-like) support system. In other words, this means in particular that the cannula is disposed in the region of a first end of the support system and that the ultrasound measuring device is disposed in the region of a second end of the support system which is opposite to the first end. The cannula and the ultrasound measuring device are preferably provided in the region of oppositely disposed ends of the support system which face away from one another.

The cannula and the ultrasound measuring device are in particular provided at oppositely disposed ends of the support system (which face away from one another). The ultrasound measuring device is preferably disposed in the region of the flow machine, in particular an electric motor of the flow machine of the support system.

According to one advantageous configuration, it is proposed that the ultrasound measuring device be disposed and oriented such that it can carry out an ultrasound measurement in the vicinity of the support system. For this purpose, the ultrasound measuring device is preferably disposed on an outer surface of the support system. For this purpose, the ultrasound measuring device is particularly preferably disposed on an outer surface, which at least partially surrounds at least one part, such as an electric motor of a flow machine of the support system. An ultrasound measurement in the vicinity of the support system end at which the ultrasound measuring device is disposed (i.e. opposite to the cannula), advantageously allows (in the implanted state in aortic valve position) the total cardiac output or the total fluid volume flow out of the ventricle into the aorta to be determined (measured) by means of an ultrasound measurement. In an ultrasound measurement in the interior of the support system or in the interior of the cannula, on the other hand, only the pump volume flow could be determined.

According to one advantageous configuration, it is proposed that the ultrasound measuring device comprise at least two ultrasound transducers. At least one of the ultrasound transducers is preferably disposed and oriented such that its main beam direction forms an angle in the range of 0° to 45° (greater than 0° and less than 45°) with a longitudinal axis of the support system or (in the implanted state) a longitudinal flow direction. Alternatively or cumulatively, it can be provided that at least one of the ultrasound transducers is disposed and oriented such that its main beam direction extends parallel to a longitudinal axis of the support system or (in the implanted state) a longitudinal flow direction. Particularly preferably, at least one other of the ultrasound transducers is disposed and oriented such that its main beam direction forms an angle in the range of 45° to 90° (greater than 45° and less than 90°) with the longitudinal axis of the support system or the longitudinal flow direction.

According to one advantageous configuration, it is proposed that the ultrasound measuring device comprise at least three ultrasound transducers. An advantageous expansion to three ultrasound transducers (possibly oriented orthogonally to one another) can advantageously contribute to being able to omit a stent that may otherwise or additionally be used for attachment, or to tolerances in the attachment having less of an effect on the measurement result. At least two ultrasound transducers (i.e. the main beam direction thereof) are preferably directed radially outward. The radial direction here refers in particular to a longitudinal axis of the support system or (in the implanted state) a longitudinal flow direction.

According to one advantageous configuration, it is proposed that at least two of the ultrasound transducers be oriented orthogonally to one another. Preferably, at least three of the ultrasound transducers are oriented orthogonally to one another. The ultrasound transducers are furthermore preferably connected to one another in a fixed or rigid manner.

The integration of the ultrasound sensor in the proximal end of the support system in particular poses unique challenges, mainly due to the high swirl of the flow observed there, so that, to achieve the best possible measurement quality, the influence of the swirl on the Doppler signal should be compensated. Orienting at least two of the ultrasound transducers orthogonally to one another advantageously allows the influence of the swirl to be taken into account. According to a particularly advantageous configuration, the arrangement is set up such that the first sonde or the first ultrasound transducer is oriented at most in the direction of the longitudinal flow (e.g. no more than 45° to the longitudinal flow) and the second sonde or the second ultrasound transducer is oriented orthogonally to the first.

According to one advantageous configuration, it is proposed that the ultrasound measuring device comprise a plurality of ultrasound transducers which are arranged to form an ultrasound array or an ultrasound matrix. This advantageously allows the entire cross-sectional anatomy of the aortic wall to be captured and/or a complete 3D vector field of the flow conditions in the aorta to be recorded. On the basis of such a 3D vector field, it is advantageously also possible to identify and take into account the influence of the swirl, so that the influence of the swirl on the Doppler signal can at least partially be compensated to achieve a best possible measurement quality.

According to one advantageous configuration, the support system further comprises a flow machine disposed between the cannula and the ultrasound measuring device. The flow machine can, for example, comprise an impeller for generating a fluid flow through the cannula toward the flow machine and an electric motor for driving said impeller.

According to one advantageous configuration, it is proposed that the support system be implantable in the aortic valve position. The support system can preferably be implanted in such a way that it intersects a plane in which the aortic valves are located. The support system can furthermore preferably be implanted in such a way that the end in the region of which the cannula is disposed faces toward the ventricle and/or is disposed in the ventricle and the end in the region of which the ultrasound measuring device is disposed faces toward the aorta and/or is disposed in the aorta.

The support system is advantageously elongated, in particular tubular, between its two ends, so that fluid transport is made possible in a limited diameter range.

Another advantageous configuration provides for the cannula to be disposed in the region of a distal end of the support system comprising an inlet opening for the fluid to be conveyed, and that the ultrasound measuring device is disposed in the region of a proximal end of the support system.

According to a further aspect, a method for determining a total fluid volume flow in the region of an implanted vascular support system is proposed, which comprises at least the following steps:

a) carrying out a first ultrasound measurement with a first orientation in the region of an end of the support system opposite to a cannula of the support system, b) carrying out a second ultrasound measurement with a second orientation different from the first orientation in the region of the end of the support system opposite to the cannula of the support system, c) determining the total fluid volume flow using the ultrasound measurements carried out in Steps a) and b).

The shown sequence of the method steps a), b) and c) is only an example and can, for example, be the result of a regular operating sequence. Steps a) and b) in particular can also be carried out at least partially in parallel or even simultaneously. The method can be carried out with a support system proposed here. The support system proposed above is advantageously also configured for carrying out a method proposed here.

In Step a), a first ultrasound measurement is carried out with a first orientation in the region, in particular in the vicinity, of an end of the support system opposite to a cannula of the support system. The orientation typically refers to the orientation of a main beam direction of an ultrasound element or an ultrasound propagation. A Doppler measurement is preferably carried out in Step a), preferably with a main beam direction that is oriented (at most) in the direction of the longitudinal flow; e.g. forms an angle of no more 45° with the longitudinal flow direction.

In Step b), a second ultrasound measurement is carried out with a second orientation different from the first orientation in the region, in particular in the vicinity, of the end of the support system opposite to the cannula of the support system. The orientation typically refers to the orientation of a main beam direction of an ultrasound element or an ultrasound propagation. A Doppler measurement is preferably carried out in Step b), preferably with a main beam direction that is oriented substantially radially to the longitudinal flow direction. The term "substantially" here includes deviations of no more than 10°.

In Step c), the total fluid volume flow is determined using the ultrasound measurements carried out in Steps a) and b). The second ultrasound measurement can advantageously be used here to at least partially compensate the influence of a rotating flow component on the first ultrasound measurement.

Different orientations (of the main beam directions) in Steps a) and b) can advantageously be achieved by at least two ultrasound transducers (i.e. the main beam directions thereof) forming an angle with one another, in particular being oriented orthogonally to one another. Step a) is preferably carried out with a first ultrasound transducer and Step b) with a second ultrasound transducer. The first ultrasound transducer and the second ultrasound transducer (i.e. the main beam directions thereof) are preferably oriented orthogonally to one another. The first ultrasound transducer and the second ultrasound transducer furthermore preferably have the same directional characteristic (side lobes, etc.). Different directional characteristics are possible in principle, but could require more complex evaluation.

Different orientations (of the main beam directions) in Steps a) and b) can advantageously also be achieved by carrying out the first ultrasound measurement and the second ultrasound measurement with a plurality of ultrasound transducers arranged to form an ultrasound array or an ultrasound matrix. The individual ultrasound transducers can be controlled (e.g. via phase delay of the ultrasound pulse) in such a way that different directional characteristics and/or orientations of the ultrasound measuring device are set. This in particular makes it possible to operate in a "scanning" manner, i.e. traverse many different angles and to determine the Doppler flow velocity for each angle. This can then be used in Step c) to determine the three-dimensional flow vector field via a signal processing.

According to one advantageous configuration, it is proposed that the ultrasound measurements carried out in Steps a) and b) be used to monitor the support system. A flow velocity that is reduced compared to reference data, for example, may provide an indication of a state of wear or clogging of the support system.

The details, features and advantageous configurations discussed in connection with the support system can correspondingly also occur in the method presented here and vice versa. In this respect, reference is made in full to the statements there for a more detailed characterization of the features.

BRIEF DESCRIPTION OF THE DRAWINGS

The solution presented here as well as its technical environment are explained in more detail below with reference to the figures. It is important to note that the invention is not intended to be limited by the design examples shown. In particular, unless explicitly stated otherwise, it is also possible to extract partial aspects of the facts explained in the figures and to combine them with other components and/or insights from other figures and/or the present description.

The figures show schematically.

DETAILED DESCRIPTION

Figure 1:
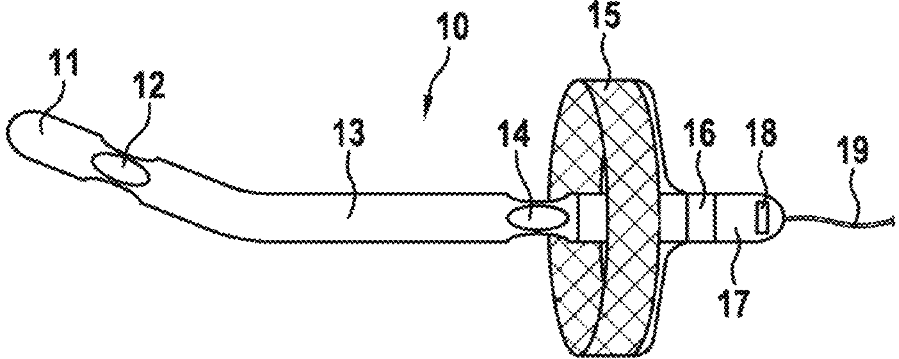
FIG. 1: an implantable vascular support system.

FIG. 1 schematically shows an implantable vascular support system 10. As an example, the support system 10 here is a left ventricular assist device (LVAD) in particular a (percutaneous) minimally invasive left ventricular assist device. The support system is advantageously configured to convey blood directly out of the left ventricle of a heart (through the atrium) into the aorta. For this purpose, the (percutaneous) minimally invasive left ventricular assist device is typically positionable or positioned centrally in the aortic valve.

The support system 10 comprises a cannula 13 and an ultrasound measuring device 18. The cannula 13 and the ultrasound measuring device 18 are provided in the region of oppositely disposed ends of the support system 10.

In other words, FIG. 1 in particular shows an LVAD for the aortic valve position with a corresponding support structure, in this case in the simple variant for positioning the flow machine (pump) in the aorta.

As an example, the support system (LVAD) 10 here comprises a tip 11, which projects into the ventricle 21 (not shown here, see FIG. 2) and can optionally contain sensors. Adjacent to this there are typically openings 12, through which blood can be taken from the ventricle 21 by the system, conveyed through the (inlet) cannula 13 to the flow machine (pump) 17 and discharged into the aorta 22, for example, via openings 14.

An example anchoring structure 15, which is connected to the flow machine 17 via a fastening element 16, can secure the system in aortic position or aortic valve position, for example, and/or help prevent shifting of the support system.

As an example, the support system 10 comprises a flow machine (pump) 17, which is disposed between the cannula 13 and the ultrasound measuring device 18. The flow machine 17 is preferably driven by an electric motor. The flow machine 17 furthermore preferably comprises an impeller (not shown here), which is located in the region of the openings 14 or extends in the region of the openings 14 in the direction of the cannula 13 and/or projects into the cannula 13. The ultrasound measuring device 18 is located at the proximal end of the system (in the region of the aorta). The ultrasound measuring device 18 is typically configured as an ultrasound sensor, as an example here in the form of a total CO flow sensor.

The support system 10 can be connected or is connected to an implanted or extracorporeal control device (not shown here) by a supply cable 19. The measuring technology with which the sensor signal of the ultrasound measuring device 18 can be evaluated and/or further processed can be implemented in the control device.

As an example, the ultrasound measuring device 18 here is disposed and oriented such that it can carry out an ultrasound measurement in the vicinity of the support system 10. For this purpose, the ultrasound measuring device 18 is disposed on an outer surface of the support system 1, for example, in particular in the region of the flow machine 17.

The ultrasound measuring device 18 comprises at least two or at least three ultrasound transducers (not shown here), for example. Preferably, at least two of the ultrasound transducers are oriented orthogonally to one another.

Figure 2:
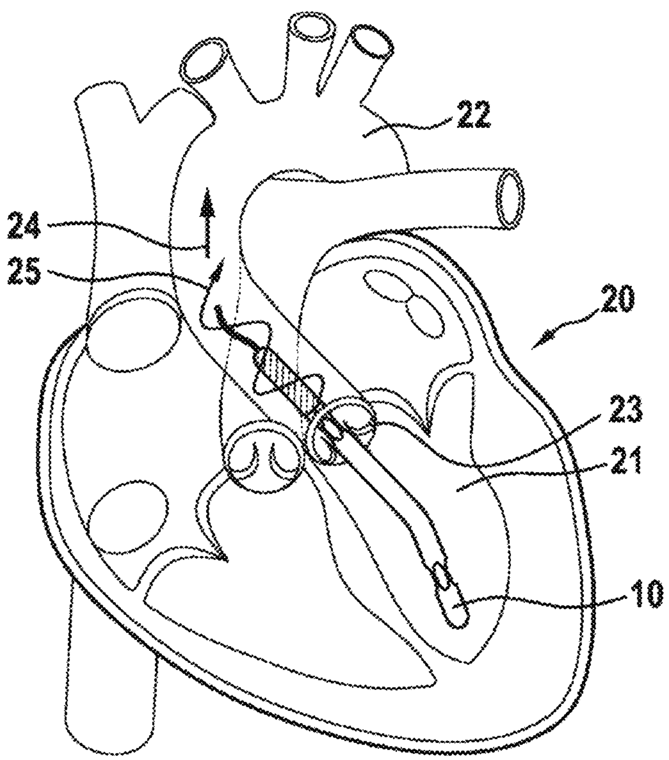
FIG. 2: a support system, implanted in a heart.

FIG. 2 schematically shows a support system 10 implanted in a heart 20. According to the illustration of FIG. 2, the support system 10 (LVAD) is implanted in aortic valve position. For this purpose, the support system 10 intersects a plane in which the aortic valves 23 are located. The support system 10 helps to convey blood from the (here left) ventricle 21 of the heart into the aorta 22. FIG. 2 thus shows the system 10, placed in aortic valve position of a heart 20 which consists of the ventricle 21 and the aorta 22 with the aortic valves 23.

The cardiac output 24, which is also referred to here as the total fluid volume flow, flows in the region of the aorta 22 and is the sum of the blood conveyed by the pump or the flow machine of the support system out of the openings 14 and a possible bypass volume flow past the support system 10 through the aortic valves 23. The spiral curve 25 indicates the swirling blood flow produced by the support system 10. Due to a very rapidly rotating impeller of the flow machine, for example, which is disposed in an impeller cage comprising the openings 14, and the mass inertia of the blood, the flow typically still has a high rotational component even after exiting the impeller cage or the openings 14, as shown in the flow line image in FIG. 3.

Figure 3:
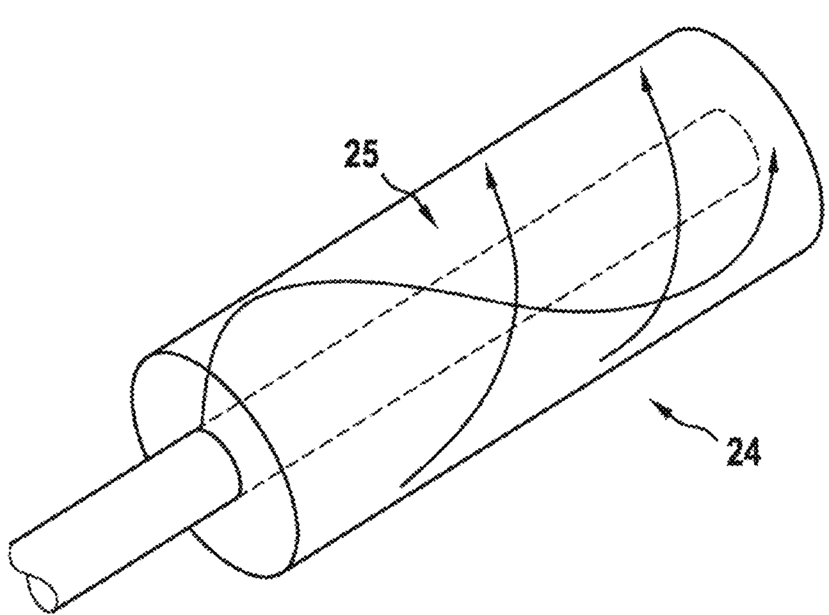
FIG. 3: an illustration of a flow line image.

FIG. 3 schematically shows an illustration of a flow line image. As discussed above, FIG. 3 illustrates that the flow still has a high rotational component even after exiting the impeller cage 14. The flow lines show a plurality of spiral curves 25 in the total fluid volume flow 24.

Figure 4:
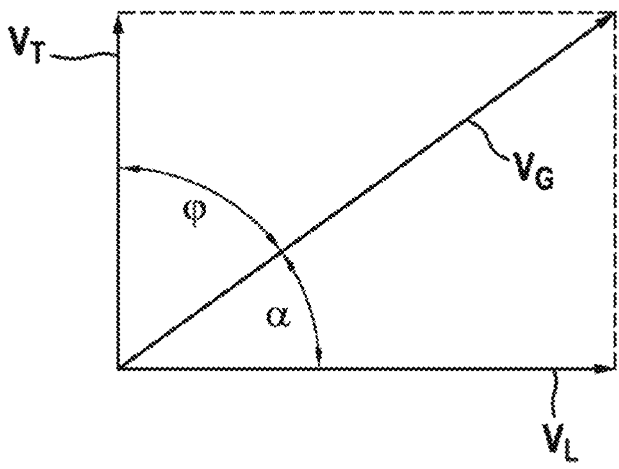
FIG. 4: an illustration of a velocity vector.

FIG. 4 schematically shows an illustration of a velocity vector. Accordingly, as shown in FIG. 4, (due to the swirl) the velocity vector of the flow $V_G$ is composed of a flow velocity $V_L$ pointing axially in the direction of the aorta and a tangentially circular rotational velocity $V_T$. Only the component $V_L$ should be used to determine the volume flow, since typically only this velocity component contributes to the volume flow along the aorta.

Figure 5:
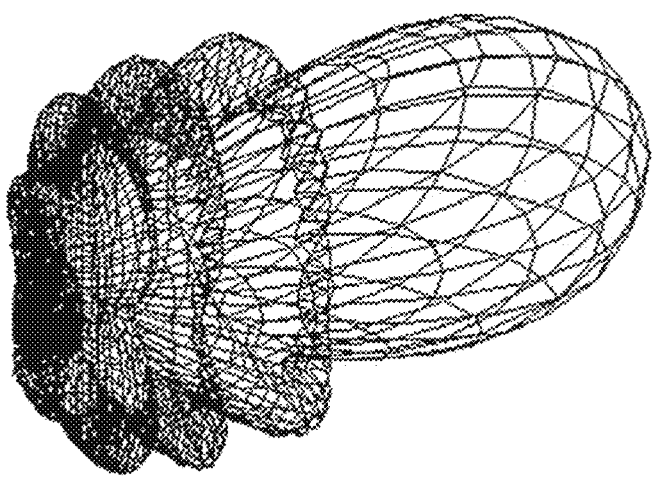
FIG. 5: an illustration of a directional characteristic of an ultrasound transducer.

FIG. 5 schematically shows an illustration of a directional characteristic of an ultrasound transducer. Since ultrasound transducers do not have a perfect directional characteristic, but instead have a lobe-shaped sensitivity, in some cases with pronounced side lobes as can be seen in FIG. 5, the ultrasound Doppler spectrum of an ultrasound transducer oriented in the direction of $V_L$ also contains components of $V_T$ (not shown here, see FIG. 4).

Figure 6:
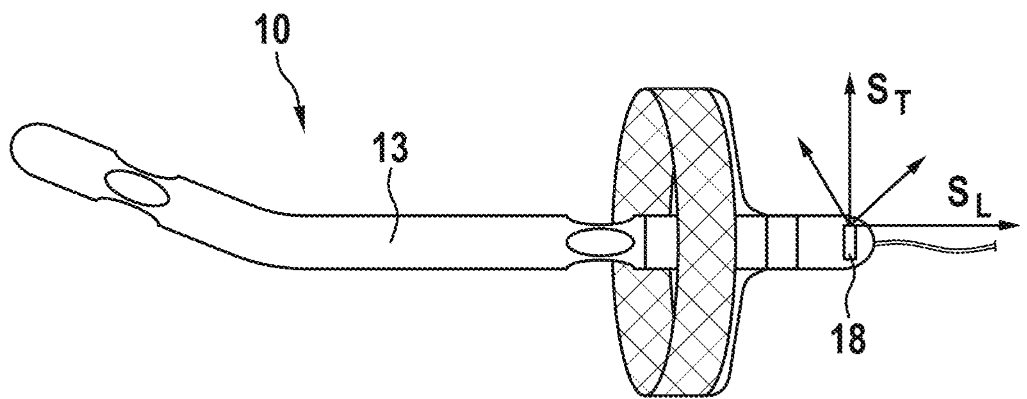
FIG. 6: a further implantable vascular support system.

FIG. 6 schematically shows a further implantable vascular support system 10. The reference signs are used consistently, so that reference can be made in full to the statements regarding the preceding figures, in particular FIG. 1.

The support system 10 comprises a cannula 13 and an ultrasound measuring device 18. The cannula 13 and the ultrasound measuring device 18 are provided in the region of oppositely disposed ends of the support system 10.

For the basic functioning of an ultrasound measurement carried out by means of the ultrasound measuring device 18, the following can be implemented:

To determine the flow velocity, a frequency shift Δf proportional to the object velocity is measured with the aid of an ultrasound transducer, in particular an ultrasound transducer. Formally, the frequency shift can be written as follows using the Doppler effect:

$$\Delta f = f_s - f_s \frac{1 - \frac{\overline{ve}_{SO}}{c}}{1 - \frac{\overline{ve}_{OB}}{c}} \tag{1}$$

Whereby $f_S$ is the transmit frequency, v is the object velocity, c is the propagation velocity and $e_{S0}$ or $e_{0B}$ is the unit vector from the transmitter to the object or object to the observer. For the transducer arrangement, the following applies $$\vec{e}_{SO} = -\vec{e}_{OB}$$

and Formula (1) can be written as $$\Delta f = \frac{2 f_s v\cos(\theta)}{c - v\cos(\theta)} \quad (2)$$

Whereby θ is the angle between the velocity vector v and the unit vector $e_{B0}$. For a propagation velocity of approx. 1500 m/s and flow velocities up to approx. 8 m/s, Formula (2) can be further simplified to:

$$\Delta f = \frac{2 f_s v\cos(\theta)}{c} \quad (3)$$

At transmit frequencies between 2-8 MHz, frequency shifts of a several hundred and a few kHz can be expected.

With regard to the integration of the ultrasound measuring device 18 in and/or on the support system 10, the following in particular must be taken into account:

Due to the geometry of the usually present flow machine (such as a pump) of the support system 10 and/or the possibly present input leads (in particular electrical input leads to the ultrasound measuring device 18), the ultrasound transducer or ultrasound transmitter cannot be oriented freely and the field of view is typically not parallel to the longitudinal flow direction and therefore also "sees" the tangential flow component.

In order to be able to determine the total fluid volume flow 24 (not shown here, see FIG. 2) or the cardiac output as accurately as possible from the Doppler shift, an arrangement which comprises at least two ultrasound transmitters or ultrasound transducers is preferable. The two ultrasound transmitters or ultrasound transducers are in particular rigid and/or orthogonal to one another.

According to a particularly advantageous configuration, the arrangement is set up such that the first sonde or the first ultrasound transducer is oriented at most in the direction of the longitudinal flow (e.g. (no more than) 45° to the longitudinal flow) and the second sonde or the second ultrasound transducer is oriented orthogonally to the first.

If, for example, the vector of the first sonde is $$\vec{e}_{SO1} = \begin{pmatrix} 1 \\ 1 \\ 0 \end{pmatrix} \frac{1}{\sqrt{2}}$$

then $$\vec{e}_{SO2} = \begin{pmatrix} -1 \\ 1 \\ 0 \end{pmatrix} \frac{1}{\sqrt{2}}$$

must advantageously be selected.

For the object velocity v, which can generally be written as a vector ($v_x$, $v_y$, $v_z$), it thus follows for the first ultrasound transducer $$\Delta f_1 = 2 f_s \frac{1}{\sqrt{2}} (v_x + v_y)$$

and for the second ultrasound transducer $$\Delta f_2 = 2 f_s \frac{1}{\sqrt{2}} (-v_x + v_y).$$

In this case, simple subtraction can lead to $$\Delta f_d = 4 f_s \frac{1}{\sqrt{2}} v_x$$

which leads to the elimination of the (tangential) velocity component $v_y$ ($v_x$ here is the longitudinal component of the flow). For other angles, $v_y$ can in particular be calculated according to the projections.

Both transmitters or ultrasound transducers having the viewing window in the x-y plane can in particular be realized by using an additional anchoring stent. To be able to look at a specific depth plane, it is furthermore advantageous to use the pulsed-wave Doppler method.

An advantageous expansion to three orthogonally positioned sondes or ultrasound transducers can advantageously contribute to being able to omit an otherwise potentially additionally inserted stent for fixing. This may minimally increase the computational effort.

An advantageous approach to being able to solve the previously described problem, according to which ultrasound transducers disposed at the end of the support system 10 opposite to the cannula 13 cannot be oriented as desired, in particular the field of view of which typically cannot be oriented (exactly) parallel to the longitudinal flow direction, is the integration of at least two ultrasound transducers disposed orthogonally to one another on the surface of the support system 1. Ideally, one transducer with a main sensitivity direction $S_L$ would be oriented parallel to $V_L$ (not shown here, see FIG. 4) and another transducer would look radially outward ($S_T$). However, such an (ideal) installation situation is (as described above) not usually practicable due to the design, for example due to the geometry of the typically present flow machine (such as a pump) of the support system 10 and/or the possibly present input leads (in particular electrical input leads to the ultrasound measuring device 18).

A particularly advantageous (practical) approach with an exemplary orthogonal orientation of two ultrasound transducers to one another is illustrated in FIG. 6. FIG. 6 illustrates (with two unlabeled arrows) an advantageous orientation of the main sensitivity directions (unit vectors $e_{so1}$ and $e_{so2}$) of the two ultrasound transducers to the main flow components $S_L$ and $S_T$. This is intended to clarify that $e_{so1}$ and $e_{so2}$ do not necessarily have to be parallel to $S_L$ and $S_T$; rather the orthogonality condition(s) and a known angle to $S_L$ are sufficient to advantageously enable the most accurate ultrasound acquisition of the flow.

Assuming an ideally focusing ultrasound transducer, the element would in particular provide no measurement signal at all in radial direction, because the transducer is oriented at a right angle to the flow $V_L$ and also at a right angle to the flow $V_T$. However, the same side lobe effects act on the transducer $S_T$ as on the transducer $S_L$. The influence of the rotating flow component $V_T$ can advantageously be compensated in a possible downstream signal processing.

Another advantage of the transducer in $S_T$ direction can be seen in this transducer (in the implanted state in aortic valve position) being able to look in the direction of the aortic wall. The aortic wall can be identifiable as a strong reflection in the received signal. Based on the approximately known speed of sound in blood, the distance between the sensor (and thus the support system) and the aortic wall can be inferred from the signal transit time between an emitted pulse and received aortic wall echo.

By integrating a plurality of (for example three) radially outward looking ultrasound transducers, the exact position of the support system in the aorta and/or the aortic cross-section can advantageously be determined with sufficient accuracy. Monitoring the position of the support system in the implanted state advantageously contributes to being able to check and/or ensure whether and/or that the transducer $S_L$ is (substantially) parallel to $V_L$ even after a longer implantation time and/or during upper body movements of the patient, or being able to determine the angle $\cos(\theta)$ in Formulas 1-3. A determination of the aortic cross-section by means of the ultrasound transducer can advantageously contribute to being able to infer the volume flow in liters per minute as accurately as possible from the flow velocity determined via a Doppler ultrasound measurement.

The approach described above in particular also has the advantage of being cost-effective. In particular, only at least two ultrasound transducers are needed and, if necessary, also only two electrical supply cables between the transducers and a (possibly extracorporeal or not also implanted) control electronics. However, this approach in particular does not allow the actual velocity vector field to be calculated and displayed. The calculations are also based in particular on the (normally justified) assumptions of a flow field that corresponds substantially to the flow field shown in FIG. 3.

Figure 7:
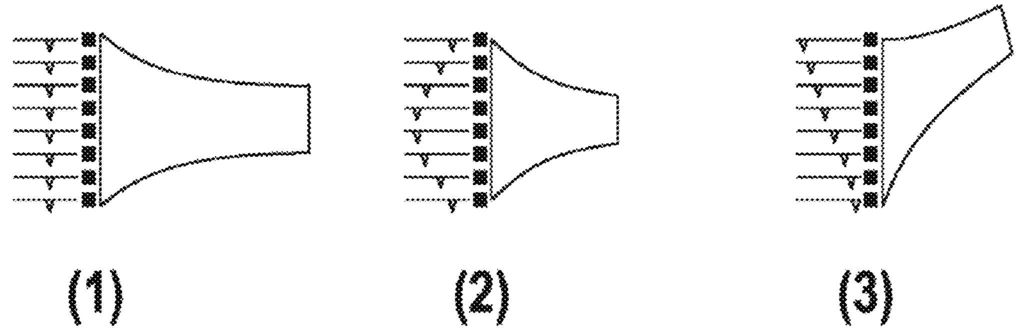
FIG. 7: an illustration of a directional characteristic of a plurality of ultrasound transducers.

FIG. 7 schematically shows an illustration of a directional characteristic of a plurality of ultrasound transducers. As an example, FIG. 7 shows different directional characteristics that can be set with a plurality of ultrasound transducers arranged to form an ultrasound array.

When the ultrasound measuring device 18 comprises a plurality of ultrasound transducers that are arranged to an ultrasound array or an ultrasound matrix, it can in particular contribute to carrying out a method referred to as 3D/4D vector flow imaging. In this case, the ultrasound measuring device preferably comprises a plurality of ultrasound transducers arranged in a matrix. Depending on the control (phase delay of the ultrasound pulse), the directional characteristic and/or the orientation of the ultrasound measuring device or the ultrasound element ($S_T$ or $S_L$ in the above example) can be changed electronically, as shown in FIG. 7 in the simplified case of a linear array. This in particular makes it possible to operate in a "scanning" manner with the matrix arrangement, i.e. traverse many different angles and to determine the Doppler flow velocity for each angle. This can be used in the signal processing step to determine the three-dimensional flow vector field.

FIG. 7 shows examples of ultrasound array control. In each case the control is shown to the left of the ultrasound elements as a plot. The line corresponds to the x-axis. A small ultrasound pulse can be seen on it. The time axis accordingly points to the left, i.e. pulses shown further to the left arrive at the ultrasound transducer later than pulses shown further to the right. FIG. 7 shows how the shape of the directional characteristic and/or the orientation of the main beam direction (of the entire ultrasound array) can, for example, be changed. On the left (1): normal characteristic, as it would, for example, also result from a massive element of the same size. In the middle (2): example of a change of the natural focus, i.e. the distance to the ultrasound transducer, in which the highest power concentration takes place and where a pulsed-wave Doppler system would also preferably place its time of observation. On the right (3): example of a linear phase delay from bottom to top so that the beam is panned.

Based on the technology of the so-called PMUT (piezoelectric micromachined ultrasound transducer) and/or CMUT (capacitive micromachined ultrasound transducer), miniaturized ultrasound arrays, which, because of their dimensions, are suitable for integration into a vascular implantable support system, are possible.

The advantage of using an ultrasound array and/or an ultrasound matrix, is that the entire cross-sectional anatomy of the aortic wall can be captured. Furthermore, a complete 3D vector field of the flow conditions in the aorta can be recorded by appropriate control of the matrix transducer.

The use of an array/matrix transducer therefore in particular represents a kind of generalization or an advantageous further development of the approach described above from at least two ultrasound transducers to 256 or more transducers (elements). At the cost of higher system complexity, this can advantageously resolve the orientation requirement and/or eliminate the need for a fixation stent.

In addition to a highly accurate calculation of the cardiac output, the vector field can also be used as a parameter for a self-monitoring of the support system. Therefore, it is to be expected that a closure of a discharge opening 14 will have significant effects on the vector field. This could possibly be determined algorithmically and used for system monitoring.

Figure 8:
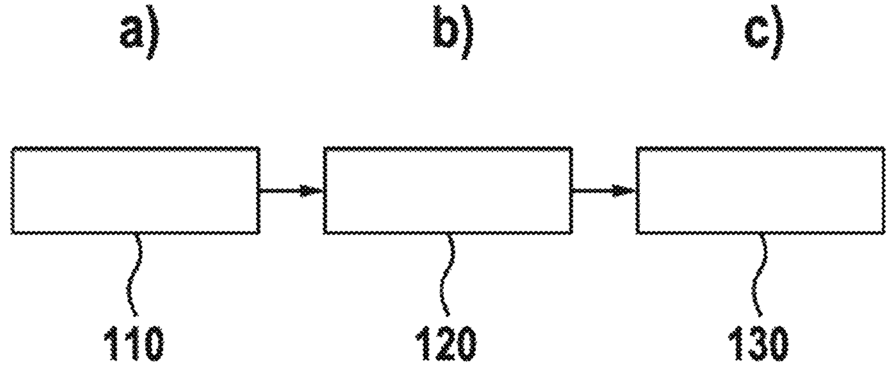
FIG. 8: a sequence of a here presented method.

FIG. 8 schematically shows a sequence of a here presented method. The method is used to determine a total fluid volume flow 24 (not shown here, see FIG. 2) in the region of an implanted vascular support system. The shown sequence of the method steps a), b) and c) with Blocks 110, 120 and 130 is only an example and can be the result of a regular operating sequence, for example. Steps a) and b) in particular can also be carried out at least partially in parallel or even simultaneously. In Block 110, a first ultrasound measurement is carried out with a first orientation in the region of an end of the support system opposite to a cannula of the support system. In Block 120, a second ultrasound measurement is carried out with a second orientation different from the first orientation in the region of the end of the support system opposite to the cannula of the support system. In Block 130, the total fluid volume flow is determined using the ultrasound measurements carried out in Steps a) and b).

The solution presented here in particular enables one or more of the following advantages:

The integration of the sensor in the proximal end of the support system can eliminate the need for additional implantation steps;

The measurement principle with orthogonal measurement directions and/or the three-dimensional vector field measurement can increase the measurement accuracy in the case of a prevailing strong swirl of the flow;

The measurement position in the aorta enables a determination of the total CO in an advantageously simple manner;

Changes in the flow profile (primarily based on the vector field method) can be used to infer changes in the pump and/or the aorta. For example, thromboses at the pump outlet or the retaining structures can have an effect on the flow field, which can be identified via a slow change in the vector field (keyword condition monitoring, predictive maintenance).

The invention claimed is:

1. An implantable cardiac support system, the system comprising:

a cannula at a distal region of the support system;

a flow machine configured to convey blood through the cannula;

an ultrasound measuring device at a proximal region of the support system, the ultrasound measuring device comprising a plurality of ultrasound transducers arranged to form an array arranged to measure blood flow in a region surrounding the support system, wherein at least two ultrasound transducers of the plurality of ultrasound transducers are oriented orthogonal to each other, wherein a main sensitivity direction of a first orthogonal transducer of the plurality of ultrasound transducers is no more than 45 degrees to a longitudinal axis of the support system and a main sensitivity direction of a second orthogonal transducer of the plurality of ultrasound transducers is 90 degrees from the first orthogonal transducer; and at least one processor programmed to receive signals from the ultrasound measuring device;

combine the signals to compensate for rotational flow induced by the flow machine; and determine a total volume flow of blood in a region of the support system in a vicinity of the flow machine based on the combined signals received from the ultrasound measuring device.

2. The support system of claim 1, wherein the ultrasound measuring device comprises at least three ultrasound transducers.

3. The support system of claim 1, wherein the at least one processor is configured to assess a direction of flow of the blood.

4. The support system of claim 1, wherein the flow machine is disposed between the cannula and the ultrasound measuring device.

5. The support system of claim 1, wherein the support system is configured to be implanted in an aortic valve.

6. The support system of claim 1, wherein the support system is elongated between a first end and a second end.

7. The support system of claim 1, wherein the cannula is disposed adjacent to a distal end of the support system comprising an inlet opening, and wherein the ultrasound measuring device is disposed adjacent to a proximal end of the support system.

8. A method for determining a total fluid volume flow of blood in a region of a cardiac support system, the method comprising:

performing a first ultrasound measurement with an ultrasound measurement device in a first orientation in a proximal region of an end of the support system that is opposite a cannula, wherein a flow machine of the support system is configured to convey blood through the cannula;

performing a second ultrasound measurement with the ultrasound measurement device in a second orientation different from the first orientation in the proximal region of the end of the support system, wherein the first orientation and the second orientation are orthogonal to each other and wherein a main sensitivity direction associated with the first orientation is no more than 45 degrees to a longitudinal axis of the support system and a main sensitivity direction associated with the second orientation is 90 degrees from the main sensitivity direction of the first orientation;

combining the first and second ultrasound measurements to compensate for rotational flow induced by the flow machine of the support system;

determining the total fluid volume flow in a vicinity of the flow machine using the combination of first and second ultrasound measurements.

9. The method of claim 8, further comprising monitoring the support system using the first and second ultrasound measurements.

10. The method of claim 8, wherein the ultrasound measurement device is positioned opposite to the cannula of the support system in the first orientation.

11. The method of claim 8, wherein the ultrasound measurement device is positioned opposite to the cannula in the second orientation.

* * * * *